United States Patent [19]

Bennett et al.

[11] Patent Number: 4,675,072
[45] Date of Patent: Jun. 23, 1987

[54] TRENCH ETCH ENDPOINT DETECTION BY LIF

[75] Inventors: Reid S. Bennett, Wappingers Falls; Linda M. Ephrath, LaGrange; Geraldine C. Schwartz, Poughkeepsie; Gary S. Selwyn, Hopewell Junction, all of N.Y.

[73] Assignee: International Business Machines Corporation, Armonk, N.Y.

[21] Appl. No.: 878,144

[22] Filed: Jun. 25, 1986

[51] Int. Cl.$^4$ .................. H01L 21/306; B44C 1/22; C03C 15/00; C23F 1/02
[52] U.S. Cl. .................. 156/626; 156/643; 156/646; 156/653; 156/656; 156/657; 156/662; 156/345; 204/298; 204/192.33
[58] Field of Search ............... 156/626, 627, 635, 643, 156/644, 646, 652, 653, 657, 656, 659.1, 661.1, 662, 663, 668, 345; 204/192 E, 298; 427/38, 39, 53.1; 118/50.1, 620, 728; 219/121 LH, 121 LJ, 121 LZ, 121 LM; 356/316, 381, 437

[56] References Cited

U.S. PATENT DOCUMENTS

| 4,289,188 | 9/1981 | Mizutani et al. | 156/626 |
| 4,328,068 | 5/1982 | Curtis | 156/626 |
| 4,377,436 | 3/1983 | Donnelly et al. | 156/626 |
| 4,394,237 | 7/1983 | Donnelly et al. | 204/192 |
| 4,415,402 | 11/1983 | Gelernt et al. | 156/626 |
| 4,430,151 | 2/1984 | Tsukada | 156/626 |
| 4,491,499 | 1/1985 | Jerde et al. | 156/626 |
| 4,493,745 | 1/1985 | Chen et al. | 156/626 |

FOREIGN PATENT DOCUMENTS 0081785 12/1982 European Pat. Off. .

OTHER PUBLICATIONS

Donnelly et al., J. Vac. Sci. Technol., 21(3), Sep./Oct. 1982, pp. 817–823.
Walkup et al., Appl. Phys. Lett. 45(4), 15 Aug. 1984, pp. 372–374.
Park & Rock, Technical Notes, pp. 214–215.
Kinsey, Amn. Rev. Phys. Chem. 1977, 28: 349–72.
Osgood et al., Laser Diagnostics Symposium, vol. 17, pp. 161–168.

Primary Examiner—William A. Powell
Attorney, Agent, or Firm—William T. Ellis

[57] ABSTRACT

Laser induced fluorescence is utilized to detect and control the reactive ion etch-through of a given layer in a wafer by detecting a large change in the concentration of a selected minor species from the wafer in the etching plasma. This selected minor species must be present in a significantly different concentration in the etched given layer compared to adjacent layers in the wafer in order to provide a proper endpoint detection. In one embodiment, when the large change in the selected minor species concentration is detected, then the RF electrodes for the reactor are automatically de-energized.

43 Claims, 5 Drawing Figures

TRENCH ETCH ENDPOINT DETECTION BY LIF

BACKGROUND OF INVENTION

The present invention relates generally to reactive ion etching endpoint detection, and more particularly, to endpoint detection via laser induced fluorescence.

Reactive ion etching or plasma etching is now typically used to delineate fine line patterns and trenches in thin films of either insulators, semiconductors, or metals by means of the removal of portions of these films in a plasma discharge. The wafer to be etched is placed in a plasma chamber into which a gas mixture is directed at a reduced pressure. In the presence of a plasma discharge generated by the application of RF energy, reactive species are generated from the feed gas by processes such as dissociative or impact ionization. Portions of the thin film are removed by chemical reaction between the reactive species and the film, as well as by bombardment of the film by ions present in the plasma. The gaseous reaction products formed by the chemical reactions and the ion bombardment of the film are continuously removed from the chamber using a vacuum pump.

One of the problems encountered in the use of reactive ion etching is the insufficient reproducibility of the etching rate. In part, this etch reproducibility problem is caused by variations in the plasma composition due to the time dependent presence of etch products, difficulties in completely controlling the surface temperature of the wafer or wafers to be etched, and batch-to-batch variation in the quantity of material to be etched, or the load. Because of this variation in the etching rate, reactive ion etching in many cases requires monitoring to detect the completion of the etching process. In this regard, it is important to detect end of the etching process in order to terminate the etch before over-etching occurs in the sublayer below the layer being etched. Such over etching is detrimental not only because it attacks the substrate or sublayer below the layer being etched, but also because it causes undercutting of the etch pattern, thereby altering the dimensions of the desired features in the etched layer.

In a typical endpoint detection scheme, a majority chemical species from the layer being etched enters the etching plasma and is observed by monitoring a relevant spectral line for that majority species as the etching process consumes the layer being etched. The time to terminate the process is inferred from changes in the intensity of this monitored majority species spectral line. The monitoring of the majority species coming from the etched layer works well in many situations where the etched layer and the sublayer therebelow are composed of different materials. However, when the composition of the etched layer and its sublayer therebelow are similar or the same, then monitoring of the majority species from the etched layer will not provide a determination of the etch endpoint. A similar problem is encountered when techniques are utilized to compensate for etch loading non-uniformities. For example, an aluminum film on a wafer is many times etched by disposing the wafer on a high purity aluminum target to thereby prevent a sudden large excess of etching species near the end of the etch process which would cause an attendant undercutting of the aluminum film. However, the use of this aluminum target prevents the determination of the etch endpoint by monitoring the majority aluminum species.

The invention as claimed is intended to remedy the above-described drawbacks. Specifically, it solves the problem of detecting the etching endpoint through a film when the majority species in the etched film and in the sublayer therebelow are the same. Additionally, the present invention solves the problem of detecting the etching endpoint through a film when the majority species in that etched film is the same as a specially designed target disposed adjacent to the wafer being etched.

SUMMARY OF THE INVENTION

Briefly, the present invention comprises a reactive ion etching apparatus capable of automatically changing the etching when a given layer of one or more integrated circuit wafers is etched through to a second layer therebelow, wherein the given layer and the second layer have different concentrations of a minor species to be monitored, with the larger concentration thereof being less than or equal to 10% of the wafer layer by weight. The apparatus comprises a plasma reactor housing containing a chamber and means for placing the wafer therein; means for generating a plasma in the chamber suitable for etching the given layer through to the second layer and for causing the minor species to enter the plasma, wherein when the given layer is etched through to the second layer, the concentration of the minor species in the plasma changes; means for directing a laser beam through the plasma in the chamber, with the laser beam having a first frequency suitable for pumping the minor species in the plasma to an excited energy state thereof, with the pumped minor species in the excited energy state then emitting a second frequency of radiation as the pumped minor species decays to a lower energy state; means for detecting only the second frequency of radiation in the chamber and for generating a control signal when a change in a parameter of the second radiation frequency is detected; and means for controlling the etching ion plasma generating means to change the plasma generation in accordance with the control signal from the detecting means.

In a preferred embodiment, the plasma generating means includes an RF source for generating the plasma from a suitable gas, and the controlling means operates to control the RF source in accordance with the control signal. The laser beam directing means may comprise means for directing a pulsed laser beam through the plasma, and the detecting means may include means for detecting the second radiation frequency only for a predetermined time period after each of the laser beam pulses.

In one embodiment of the present invention, the given layer being etched is an Al film with a Cu minor species therein, and a second layer is disposed therebelow which does not contain Cu as a minor species. In this embodiment, a plasma containing Cl is utilized and the laser beam directing means includes means for directing the laser beam with a first frequency which is suitable for pumping CuCl.

In a further embodiment of the present invention, the given layer to be etched is $SiO_2$ without Al doping, and the second layer therebelow includes a plurality of Al alloy studs therein with Al comprising the minor species to be monitored. In this embodiment, a plasma containing F is utilized and a laser beam with a first frequency suitable for pumping an Al minor species of AlF is utilized.

In yet a further embodiment of the present invention, the given layer to be etched is chosen from a group of Si with As as the minor species, and Si with P as the minor species. When the given layer is Si with As as the minor species, a plasma is utilized which causes the As minor species to form a species in the plasma from the group consisting of AsCl and AsF.

In yet a further embodiment of the present invention, polycrystalline silicon which is heavily doped with a minor species of B is utilized and a second layer is disposed therebelow containing a B minor species therein with a concentration that is at least 50% less than in the given layer.

The present invention further comprises a method for automatically controlling the etching of an integrated circuit wafer in the chamber of a reactive ion etching reactor when a given layer of wafer is etched through to a second layer therebelow, wherein the given layer and the second layer have different concentrations of a minor species, with the layer concentration thereof being less than or equal to 10% of the wafer layer by weight. The method comprises the steps of etching the wafer in the etching reactor with an etching ion plasma suitable for etching the given layer through to the second layer and for causing the minor species to enter the plasma, wherein when the given layer is etched through to the second layer, the concentration of the minor species changes; directing a laser beam through the plasma in the chamber, with the laser beam having a first frequency suitable for pumping the minor species in the plasma to an excited energy state thereof, with the pumped minor species in the excited energy state then emitting a second frequency of radiation as the pumped minor species decays to a lower energy state; detecting a second frequency of radiation in the chamber; generating a control signal when a change in a parameter of the second frequency of radiation is detected, thereby indicating that the given layer has been etched through to the second layer; and changing the plasma generation in the chamber in accordance with the control signal.

The present invention also encompasses a variety of method embodiments thereof which are coincident with the previously set forth apparatus embodiments.

DETAILED DESCRIPTION OF THE PREFERRED EMBODIMENT

The present invention sets forth a method and a means for modifying the etching in a reactive ion etching device in accordance with a change in concentration of a minor species as a given layer in the wafer is etched through to a second layer therebelow. It has been discovered that minor species of less than 0.1% of a wafer layer by weight can be detected by the laser-induced fluorescence technique utilizing a pulsed laser beam. It has been discovered that such minor species can be detected with unusually high sensitivity using the LIF technique, despite the pulsed nature of the LIF laser beam required due to the relatively strong radiation background from the plasma emission.

In this regard, the present invention broadly covers the monitoring by laser induced fluorescence of a minor species in one or more layers of a wafer being etched in an etch reactor in combination with the use of a control signal generated in accordance with this minor species monitoring to control the etching in the etch reactor. The invention will be described in the context of a number of different examples. It should be noted that these examples are set forth, not by way of limitation, but to illustrate a number of different aspects of the present invention.

Figures 1, 2, 3:
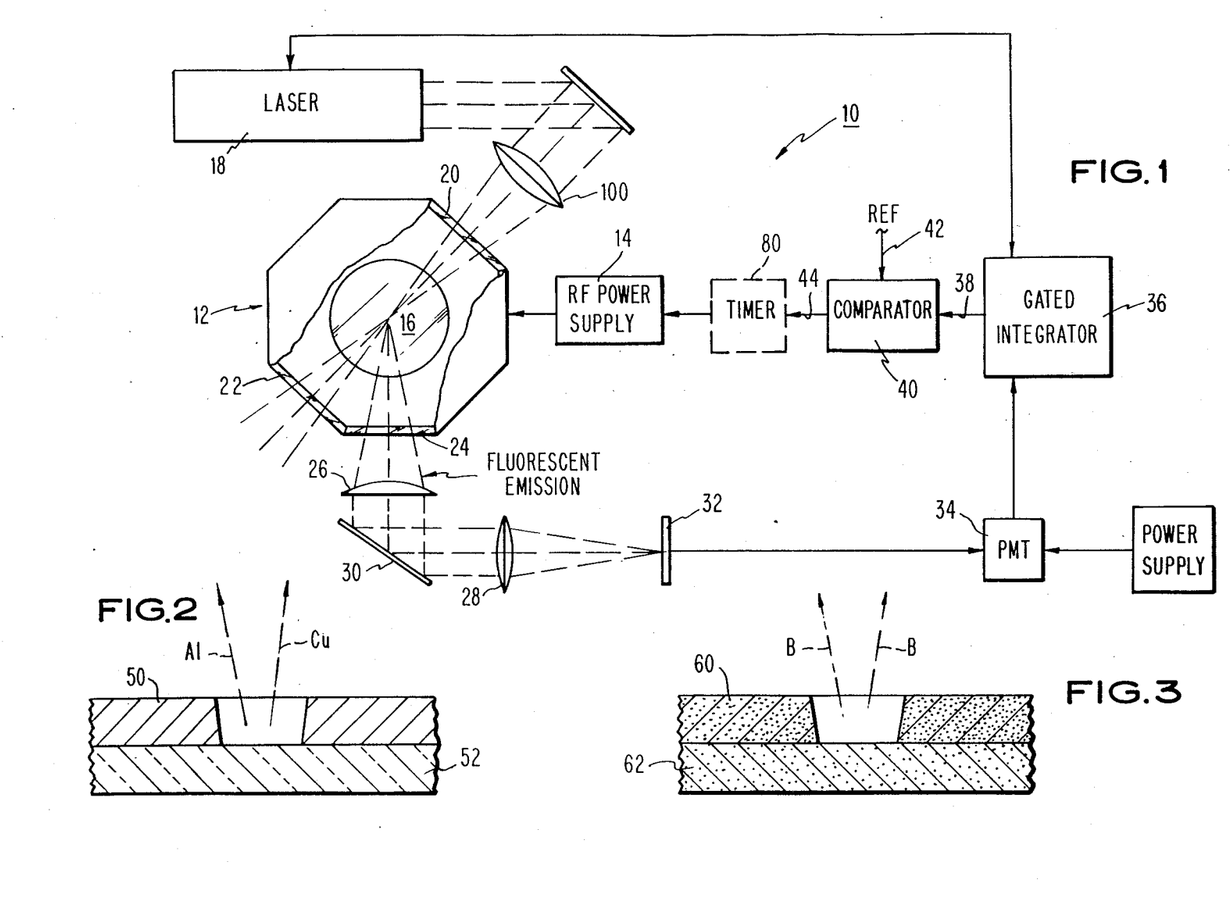
FIG. 1 is a schematic block diagram of one embodiment of the present invention.
FIG. 2 is a schematic cross-section of an Al wafer layer which may be etched utilizing the present invention.
FIG. 3 is a schematic cross-sectional diagram of a set of polysilicon layers which may be etched utilizing the present invention.

Referring now to FIG. 1, there is shown one embodiment of a system 10 for the preferential etching of monocrystalline silicon or other semiconductor material (in regions not masked by silicon dioxide or silicon nitride) and which may be utilized to implement the present invention. The system 10 includes a plasma etching reactor 12, which may be implemented by any of a variety of currently available plasma or reactive ion etching devices. One such apparatus is the parallel-plate reactive ion etcher described in the article by J. Lechaton and J. L. Mauer in the Proc. of the Symposium on Plasma Etching and Deposition Electrochem Soc., Vol. 81-1, pp. 75-85, 1981. A standard planar-type reactor 12 with parallel plate electrodes is shown in the Figure. The chamber of etching reactor 12 is typically pumped down to a vacuum equal to or less than $5 \times 10^{-6}$ torr. This reactive etching chamber is then backfilled with a gas mixture appropriate to forming a desired plasma, for example, argon and chlorine with the chlorine being 3% to 7% of the argon-chlorine gas mixture. The resulting gas pressure is about 30 millitorr. Other gases, such as $SF_6/Cl/He$ and $CF_4$ can also be used in this mixture.

In the system 10 this example, a 13.56 MHz RF power supply 14 is connected to the reactor 12 to provide the RF power to the electrodes in the etch reactor chamber. An integrated circuit wafer 16 is shown positioned in the etch reactor. It is, of course, understood that a multi-wafer etch reactor may be utilized in place of the single wafer etch reactor shown in FIG. 1. One or more gas inlets are provided (not shown) in order to insert the suitable gas mixture into the etch reactor chamber 12 in order to generate the desired plasma in the chamber.

In order to obtain laser-induced fluorescence (LIF) detection, a laser 18 is provided to direct a laser beam through a set of opposing windows 20 and 22 in the etch reactor chamber 12. A variety of portable and inexpensive lasers are available on the market which can be utilized to implement the present invention. The type of laser utilized will depend on the wavelength needed to pump the minor species to be monitored in accordance with the present invention. By way of example, and not by way of limitation, a Laser Science DCR1 nitrogen-pumped dye laser may be utilized as the laser 18. In the alternative, an Nd:YAG laser comprising a PDL1 dye laser pumped by a Quanta Ray DCR2 layer may be utilized with frequency doubling using a KD * P crystal. The windows 20 and 22 may be realized simply by standard quartz windows, which are capable of passing radiation in the range of 170 nm to 4500 nm.

As noted above, the spectral envelope of the light from the laser beam is chosen to overlap an absorption line of a selected minor species to be monitored. Directing the laser beam 18 with the appropriate spectral envelope through the plasma in the etch reactor chamber 12 causes the selected minor species in the plasma to be excited to a predetermined upper energy state. These excited minor species molecules then decay down to a lower energy state and emit a second frequency of radiation during this decay. This second frequency of radiation (fluorescence) is indicative of the presence of the minor species in the plasma. The relative intensity of this second frequency of radiation is indicative of the concentration of the minor species in the plasma.

In order to detect this second frequency of radiation, a third window 24 of suitable material is provided in the etch reactor chamber 12. Typically, this window 24 will be located at some angle relative to the line between the two windows 20 and 22 in order to substantially reduce the detection of scattered light from the laser excitation source 18. The actual means for detecting this second frequency of radiation is not critical. By way of example, a set of lenses 26 and 28 in combination with a mirror 30 may be utilized to provide radiation obtained from this third window 24 to a detector such as a photomultiplier tube 34. By way of example, the photomultiplier tube made by RCA may be utilized. In order to remove other extraneous frequencies from the light obtained from the window 24, a monochromator or a filter 32 may be utilized. Generally, this monochromator or filter 32 is disposed between the lens optics 28a and the photomultiplier tube 34. By way of example, this filter 32 may be realized by a dielectric filter with a 5 nm band pass.

In order to improve the signal-to-noise ratio of the second frequency signal, a pulsed laser 18 is used in combination with a gated integrater 36 which is connected to receive the signal from the photomultiplier 34 and which is triggered by a control signal from the laser 18. A typical laser pulse duration is from 1 to 50 nanoseconds. The gated integrator 36 is synchronized to the beginning of the laser pulse and holds its gate in a conductive state for approximately 50 nano-seconds. This gating removes a significant amount of the background interference from the signal.

The present system is designed to monitor a parameter of this second frequency of radiation in order to determine when a change has occurred in the etching plasma composition in the etch reactor chamber 12. Typically, this plasma composition change in the reactor will be the result of a given layer on the wafer being etched through down to a second layer therebelow. In general, the parameter that is monitored is the intensity of the second frequency of radiation that is detected by the photomultiplier 34. In order to detect a change in this intensity parameter of the second frequency of radiation, the gated signal from the integrater 36 is provided via a line 38 to a comparator 40. The comparator 40 compares the amplitude of the electrical signal from the integrater 36 to a reference provided on line 42. The comparator 40 generates a signal on line 44 to control the operation of the RF power supply 14 in accordance with this comparison.

The operation of the foregoing apparatus will now be described for the etching of a given layer of a wafer down to a second layer set therebelow, wherein the given layer and the second layer have different concentrations of a predetermined minor species, with the larger of the concentrations thereof being less than or equal to 10% of either of the wafer layers by weight. The wafer to be etched is placed in the reactor chamber 12, and an appropriate gas mixture is provided to the chamber to facilitate plasma generation. Then, RF power is provided to the chamber in the well known manner by the RF power supply 14 to generate a desired etching plasma in the chamber for etching the given layer of the wafer 16. Majority and minor species atoms and molecules from the wafer layers being etched enter the plasma during the etching process. As this etching operation proceeds, a laser beam from the laser 18 with an appropriate wavelength envelope for exciting a selected minor species is directed through the plasma in the reactor chamber 12 via the windows 20 and 22. This laser beam excites the selected minor species in the plasma to an excited energy state. These excited minor species molecules then decay to a lower energy state and emit the second frequency of radiation during this decay. This second frequency of radiation is brought out from the etch reactor chamber 12 via the optics 26, 28, and 30 to the photomultiplier 34 and causes the photomultiplier to generate a signal indicative of a certain range of concentrations for the minor species in the plasma. When this given layer is etched through to the second layer therebelow, a relatively sharp change in the concentration of the minor species in the plasma in the reactor chamber 12 takes place because of the difference in concentration of the minor species in the given layer and in the second layer. This change in the minor species concentration in the plasma results in a change in the intensity of light detected at the photomultiplier 34, and thus a change in the electrical signal on line 38 applied to the comparator 40. The comparator 40 then operates to generate a control signal 44 to turn off the RF power supply 14, thereby stopping the generation of the plasma in the etch reactor 12.

Various examples of the operation of the present invention will now be described in the context of specific wafer structure.

EXAMPLE 1

During the reactive ion etch processing of aluminum films, wafers are typically mounted on a high purity aluminum target to avoid large changes in loading during the tail end of the etch process. The high purity aluminum target prevents a sudden excess of etching species near endpoint and thereby prevents the undercutting associated with changes in the etch load. However, because the aluminum target contributes a large background of aluminum in the plasma concentration of the Al species cannot reliably indicate the etch endpoint for the Al film. However, standard Al films have approximately 2–5% copper therein as a dopant. When a standard Cl containing plasma, i.e., $BCl_3$ plasma, is utilized, then a Cu minor species of CuCl is generated and becomes part of the plasma during the etching of the Al film.

Because of the very low concentration of the Cu in the Al alloy, a sensitive detection of the CuCl in the plasma was considered unlikely. However, when a nitrogen pumped dye laser at 100 Kwatt power was directed through the plasma in the chamber 12, and was tuned to the 515.2 nm line in the CuCl absorption band (which corresponds to the $(1,0)A^1\pi\text{-}X^1\epsilon$ transition), then very good sensitivity was obtained by monitoring the resultant fluorescence. In this particular experiment, the $[CuCl]_x$ emission band at 538.1 nm which corresponds to the (1,2,)A-X transition was monitored. This transition wavelength was advantageous because it is well separated from the laser wavelength. It should be noted that the sensitivity of this CuCl line was very good despite the fact that the laser pulsing in combination with gated detection was utilized in order to minimize background emission from the plasma.

Accordingly, the present technique was utilized to determine the etch endpoint by monitoring the CuCl concentration in the plasma via the LIF detection of a particular laser transition line therefor. This technique of monitoring a transition from a minor species in the layer is advantageous in that it is insensitive to the interference generated by the aluminum target and thus provides a very accurate endpoint. Additionally, this minor species monitoring technique provides an endpoint detection which is usable in a multiple wafer tool where a reflectance monitoring technique would only indicate an etch rate for a single spot on a single wafer. In contrast to reflectance monitoring, because the plasma composition is determined by the etching of all of the wafers present in the reactor, the CuCl transition detection technique disclosed herein may be utilized to determine when the last wafer is fully etched, i.e., when no more $[CuCl]_x$ is generated.

As noted previously, the signal on line 38 is an electrical signal indicative of the concentration of the CuCl in the plasma. When the amplitude of this signal falls below a certain predetermined level, then the given layer of the wafer or wafers present in the reactor chamber 12 are considered to be etched through. Accordingly, when the signal on line 38 drops to this predetermined level, it is desired to generate a control signal on line 44 to turn off the RF power supply 14. The comparator 40 operates to generate this control signal on line 44 after comparing the amplitude of the signal on line 38 to an appropriate reference signal on line 42. By way of example, for the detection of the etch endpoint for an Al layer with 4% Cu, the reference signal on line 42 should be less than or equal to 5% of the initial signal value on line 38. Accordingly, when the level of the signal on line 38 is determined by the comparator to be less than the 5% reference signal on line 42, then the comparator 40 generates the control signal on line 44 to turn off the RF power supply 14.

FIG. 2 provides a schematic cross-sectional representation of a given layer 50 of Al with 4% Cu and with a second layer 52 therebelow of $SiO_2$. Various species of Al and Cu are shown entering the plasma during the etching of the given layer 50.

EXAMPLE 2

Referring now to FIG. 3, there is shown a schematic cross-sectional diagram of a given layer 60 of polycrystalline silicon with a heavy doping of boron of on the order of $10^{20}$ atoms/cm$^3$ being etched through to a second layer 62 therebelow of polycrystalline silicon with a low boron doping of on the order of $10^{15}$–$10^{16}$ atoms/cm$^3$. Various boron species are shown entering the plasma. It can be seen that in this etching situation, the minor species of boron is present in both layers 60 and 62. However, the concentration of the boron minor species in the layer 62 is reduced by at least 50% below the concentration of the boron in the given layer 60. Accordingly, in order to determine the etching endpoint through the given layer 60, the reference value on line 42 of the comparator 40 is provided with a value which is decreased by at least 50% from the initial value of the signal on the line 38 when etching of the given layer is first begun. When the amplitude of the signal on line 38 drops below this 50% reference signal value on line 42, then the comparator 40 generates the control signal on line 44 to turn off the RF power supply 14. In the Example, a 100 Kwatt power laser beam, with a wavelength of 272.0 nm is used to pump the $\tilde{X} \rightarrow \tilde{A}$ transition of BCl. The second frequency of radiation was obtained by monitoring the 284.75 nm wavelength for the $\tilde{A} \rightarrow \tilde{X}$ transition. Alternatively, a laser beam with a 195.75 nm wavelength could be used to pump the $\tilde{X} \rightarrow \tilde{A}$ transition of BF. The second frequency of radiation is obtained by monitoring the 201.1 nm wavelength for the $\tilde{A} \rightarrow \tilde{X}$ transition.

EXAMPLE 3

Figures 4, 5:
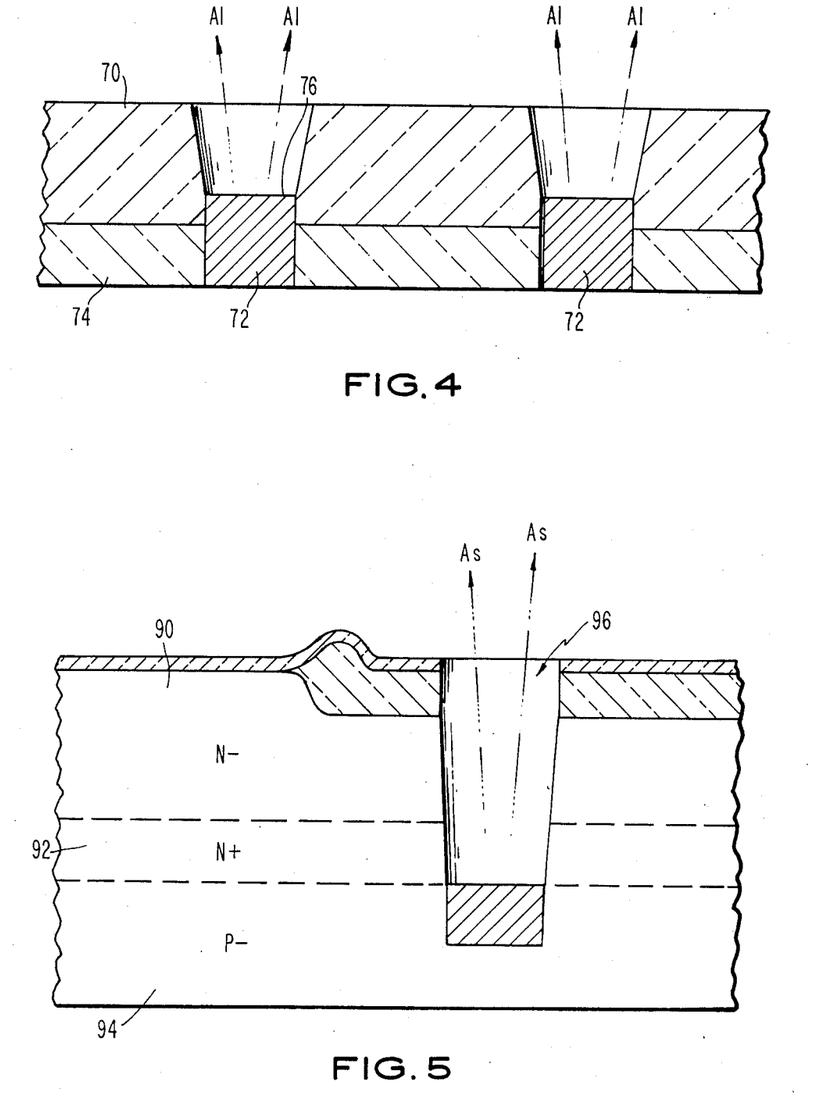
FIG. 4 is a schematic cross-sectional diagram of a chip being etched down to Al studs.
FIG. 5 is a schematic cross-sectional diagram of a silicon wafer being etched through a doped subcollector.

Example 3 relates to the endpoint detection for a vertical wiring process utilizing metallic studs. In this regard, it is important to stop the etching as soon as all of the metallic studs are exposed to prevent the capacitance and insulation problems that result from overetching into the surrounding layer. FIG. 4 is a schematic cross-sectional diagram showing a given layer 70 of $SiO_2$ to be etched through down to metallized studs 72 of, for example, aluminum. The studs 72 are typically set in a layer 74 of, for example, $SiO_2$. In this particular instance, the aluminum studs 72 constitute a very small portion of the entire layer 74 and thus constitute the minor species to be monitored. In operation, when the plasma etches through the given layer 70 down to the studs 72, various Al species enter the plasma. The amount of Al minor species in the plasma can be monitored to determine when the etching has reached the first studs, and to determine when all of the studs have been exposed.

In the particular example of FIG. 4, an F containing plasma is utilized to convert the surface 76 of the Al alloy studs 72 to AlF. This AlF surface 76 is sputtered off by the energetic ions in the plasma. The presence of the AlF minor species may be monitored by tuning the laser 18 to the 227.47 nm wavelength for AlF (transition $\tilde{A} - \tilde{X}$) and then detecting the 231.64 nm wavelength for the $\tilde{X} - \tilde{A}$ transition fluorescence.

In order to detect when the plasma etching has reached the first Al studs 72, the reference value on line 42 to the comparator 40 may be set to a level which is on the order of 10% greater than the amplitude of the detected signal on line 38 when it is etching through the $SiO_2$ given layer 70. When the amplitude of the signal on line 38 increases above the reference level on line 42, then the comparator 40 generates a signal on line 44. This signal on line 44 may be utilized to energize a timer 80, shown in dashed line representation in FIG. 1. The timer 80 may be used to count for a predetermined period of time equal to the time it takes to expose all of the studs after the first stud has been exposed. When the timer 80 has counted to this predetermined time value, it then may generate a signal to turn off the RF power supply 14. In the alternative, an integrating logic circuit (not shown) could be connected directly to line 38 and could be utilized, after the comparator 40 has determined that the first stud has been exposed, to integrate the value of the signal on line 38 to determine when the amplitude of that signal has reached a constant value indicating that all of the studs 72 have been exposed.

EXAMPLE 4

The final example relates to the detection of the etching endpoint through a doped subcollector region. FIG. 5 is a schematic cross-sectional diagram of a wafer with such a subcollector structure. The wafer may be, for example, a silicon wafer or a gallium arsenide wafer with either p type or n type subcollector doping. In the example shown in FIG. 5, a top layer 90 of N− doped silicon is illustrated, with a subcollector layer 92 of N+ doped silicon disposed therebelow. This N+ subcollector layer 92 comprises the given layer to be etched through. A second layer 94 set below the given layer 92 comprises P− doped silicon. It is desired to etch a trench 96 through the subcollector given layer 92. In the wafer in Example 4, the silicon dopant for n type doping of the layers 90, 92 and 94 is generally either P or As. A typical As doping concentration for the subcollector given layer 92 is $10^{20}$ atoms/cm$^2$. Likewise, a given doping concentration for the second layer 94 therebelow is $10^{15}$–$10^{16}$ atoms/cm$^2$.

With respect to the structure of FIG. 5, it is important that the trench 96 be etched completely through the N+ subcollector given layer 92 in order to avoid electrical leakage. Current techniques for monitoring the etch rate through such a subcollector region include laser interferometry on the wafer surface and the measurement of the etch time as a means of estimating etch depth. However, because of the varying thicknesses of the oxides and photoresists utilized in forming the wafer, the depth of the subcollector given layer 92 below the surface varies. Accordingly, since both of these techniques monitor the etch depth, they are inherently unreliable for determining the etch endpoint through the subcollector given layer 92. Note that in this structure the major species of Si does not change during the trench etch.

In order to monitor and detect the endpoint of the etch through the given layer 92 in accordance with the present invention, the concentration of a minor species from the subcollector is monitored in the plasma. In the Example of FIG. 5 with an As-doped subcollector given layer 92, etching in a halogen plasma (i.e., $CCl_2F_2$ or $CClF_3$) produces a trace quantity of AsCl or AsF in the plasma when the trench etch reaches the subcollector given layer 92. Note that very small amounts of As of on the order of $10^{14}$ atoms/cm$^3$ are in layer 90 and in layer 94. Accordingly, very small amounts of AsCl or AsF may be generated during the etching of the epi layer 90 above the subcollector given layer 92, or during the etching of the substrate layer 94 below the subcollector given layer 92. However, since the dopant concentration in the subcollector given layer 92 is $10^6$ time greater than in the surrounding layers, a signal tuned to an appropriate transition for AsCl or AsF will increase rapidly as the subcollector given layer 92 is reached, and then drop precipitously as the given layer 92 is etched through.

In Example 4, an Nd:YAG laser system made by Quanta-Ray can be focussed on a point approximately 1 cm above the target in the etch reactor. The laser may be tuned to a wavelength corresponding to an electronic state of the minor species being monitored. In the example for As doping, a laser pumping wavelength of 244.63 nm may be utilized to detect a minor species of AsCl at the 249.98 nm emission wavelength. Alternately, a laser pumping wavelength of 239.88 nm may be utilized to detect a minor species of AsF at the 248.03 nm emission wavelength.

As a further alternative, minor species As atoms may be used for the endpoint detection. In this regard, during etching the As volatilizes as AsF and AsCl$_x$, and a portion of these species is fragmented back to As in the plasma via plasma dissociation. It has been discovered that the As atom $4p^3\ ^4S_{3/2} \rightarrow 5s\ ^4P_{3/2}$ transition at 193.75927 nm is coincident with the 193 nm ArF excimer laser output. The second frequency of detection for this state would then be the 245.6529 nm ($5s\ ^4P_{3/2} \rightarrow 4p^3\ ^2D_{5/2}$ transition) or the 303.2847 nm ($5s\ ^4P_{3/2} \rightarrow 4p^3\ ^2P_{3/2}$ transition). The As atoms present in the plasma can be detected with extremely high sensitivity using these transitions.

With reference to FIG. 1, the RF power supply 14 should be turned off when the minor species being monitored drops in concentration by at least 50%. In order to detect this 50% drop in concentration, the reference level on line 42 is set to a level which is approximately 50% less than the amplitude of the signal on line 38 when it is etching in the subcollector given layer 92. Accordingly, when the amplitude of the signal on line 38 drops below the 50% reference level on line 42, the comparator 40 generates a control signal on line 44 to turn off the RF power supply 14.

It can be seen from the above examples that the present endpoint detection apparatus and method can be utilized for both Si wafers, GaAs wafers, or other III-V semiconductor wafers. With this technique, it is possible to monitor selected minor species which have been converted from the bulk layers being etched into the gaseous plasma. This technique is highly sensitive to the chemical composition of each etch layer and does not rely on any form of measurement of the etch depth.

The apparatus set forth in FIG. 1 exercises control over the etch reactor chamber 12 by turning off the RF power supply 14. It should be noted, however, that etch control may also be exerted by controlling the flow of etch gases into the etch reactor chamber 12.

Typically, the laser beam will be directed through the etch chamber 12 at a height of approximately 5 cm above the wafer being etched. The location of the laser beam at this height above the wafer will provide a generalized picture of the plasma which is very useful for batch type reactors. However, it may be desirable to direct the laser beam at a height which is very close to the wafer surface, i.e., approximately 2 mm or less, in order to obtain a localized monitoring of the plasma above a particular region on the wafer. It should be noted that for high pressure single wafer reactors where the electrode plates are separated by only 3 mm, this relatively low height for the laser beam may be necessary. In contrast, low pressure wafer reactors typically have electrode plates which are separated by 50 mm, and thus permit a variety of laser beam heights above the wafer.

It should be noted that it may be desirable to scan the laser beam across the wafer in order to get detection samples of the plasma fluorescence at various points therein. Such laser beam scanning may be necessary if the laser beam is disposed very close to the surface of the wafer in order to monitor the plasma over a variety of separated localized etch regions. Such a technique would provide extremely high sensitivity for each etch region being monitored. Laser beam scanning can be implemented simply by mechanically varying the position of the beam optics used to direct the beam through the window 20 of FIG. 1.

In general, laser beam focusing is not necessary for etch endpoint detection. However, such focusing does improve spatial resolution and would be useful where localized plasma monitoring is desired.

The present technique may also be utilized to adjust the etching rate in the etch reactor 12. The etching rate may be controlled by controlling the gas inlets into various points in the etch reactor chamber or by varying the RF intensity at various points in the reactor chamber 12 to thereby change the etching at those points in the chamber.

In one embodiment, the etch reactor chamber 12 could include at least 2 closable gas inlets into the chamber, each for providing a suitable gas mixture into a different predetermined volume of the chamber. These gas inlets would then be regulated to control the amount of gas being applied to the reactor chamber to thereby control the etching therein.

In order to monitor the etching uniformity in the reactor chamber 12, the laser beam 18 would include a focusing lens 100 for focusing the laser beam to a predetermined point in the plasma in the chamber 12. A standard scanning apparatus would then be utilized to mechanically scan this lens 100 and any other focusing optics to thereby scan the focused point over a plurality of predetermined volumes in chamber 12. The detecting apparatus would then include means for mechanically moving the detecting optics to thereby monitor the fluorescence from this scanned focused point in the chamber 12. The detecting means would further include means for comparing the intensity of the second frequency of radiation obtained for each of the focused points (or any integrated value therefor) in a given one of the plurality of predetermined volumes in the plasma to a reference value, and then generating a signal indicative of this comparison as a control signal. This control signal would then be applied to regulate the amount of gas provided through the at least two gas inlets to thereby obtain etching uniformity. This apparatus could also be used to provide a profile of the etch concentration in the reactor chamber 12.

While the invention has been illustrated and described with respect to preferred embodiments of this invention, it is to be understood that the invention is not limited to the precise construction herein disclosed, and the right is reserved to all changes and modifications coming within the scope of the invention, as defined in the appended claims.

We claim:

1. A reactive ion etching apparatus capable of automatically changing the etching when a given layer of one or more integrated circuit wafers is etched through to a second layer therebelow, wherein said given layer and said second layer have different concentrations of a minor species to be monitored, with the layer concentration thereof being less than or equal to 10% of the wafer layer by weight, comprising:
a plasma reactor housing containing a chamber and means for placing said wafer therein;
means for generating an etching ion plasma in said chamber suitable for etching said given layer through to said second layer and for causing said minor species to enter said plasma, wherein when said given layer is etched through to said second layer, the concentration of said minor species in said plasma changes;
means for directing a laser beam through said plasma in said chamber, with said laser beam having a first frequency suitable for pumping said minor species in its plasma to an excited energy state thereof, with said pumped minor species in said excited energy state then emitting a second frequency of radiation as said pumped minor species decays to a lower energy state;
means for detecting only said second frequency of radiation in said chamber and for generating a control signal when a change in a parameter of said second radiation frequency is detected; and
means for controlling said etching ion plasma generating means to change the plasma generation in accordance with said control signal from said detecting means.

2. An apparatus as defined in claim 1, wherein said plasma generating means includes at least one closable gas inlet into said chamber for providing a suitable gas for forming said ion plasma, and further includes an RF source for generating said plasma from said suitable gas; and
wherein said controlling means controls at least said RF source in accordance with said control signal.

3. An apparatus as defined in claim 1, wherein said laser beam directing means comprises means for directing a pulsed laser beam through said ion plasma; and
wherein said detecting means includes means for detecting said second radiation frequency only for a predetermined time period after initiation of each of said laser beam pulses.

4. An apparatus as defined in claim 3, wherein said detecting means includes means for generating a control signal when the intensity parameter of said second frequency of radiation changes by a predetermined amount.

5. An apparatus as defined in claim 4, wherein said given layer of said wafer is an Al film with Cu as said minor species, and said second layer does not contain Cu as a minor species.

6. An apparatus as defined in claim 5, wherein said plasma generating means includes means for generating a plasma containing Cl; and
wherein said laser beam directing means includes means for directing said laser beam with a first frequency which is suitable for pumping a Cu minor species of $[CuCl]_x$ to an upper energy state.

7. An apparatus as defined in claim 6, wherein said detecting means includes means for generating said control signal when the intensity parameter of said second frequency of radiation decreases to less than 5% of its initial value in etching said given layer.

8. An apparatus as defined in claim 7, wherein said plasma generating means includes at least one closable gas inlet into said chamber for providing a suitable gas for forming said ion plasma, and, further includes an RF source for generating said plasma from said suitable gas; and
wherein said controlling means controls at least said RF source in accordance with said control signal.

9. An apparatus as defined in claim 4, wherein said given layer of said wafer is $SiO_2$ without Al doping, and said second layer includes a plurality of Al alloy studs therein, with Al comprising said minor species to be monitored.

10. An apparatus as defined in claim 9, wherein said plasma generating means includes means for generating a plasma containing F; and wherein said laser beam directing means includes means for directing said laser beam with a first frequency which is suitable for pumping an Al minor species of AlF to an upper energy state.

11. An apparatus as defined in claim 10, wherein said detecting means includes means for generating said control signal when the intensity parameter of said second frequency of radiation increases to a constant value.

12. An apparatus as defined in claim 11, wherein said plasma generating means includes at least one closable gas inlet into said chamber for providing a suitable gas for forming said ion plasma, and further includes an RF source for generating said plasma from said suitable gas; and wherein said controlling means controls at least said RF source in accordance with said control signal.

13. An apparatus as defined in claim 4, wherein said given layer is chosen from the group consisting of Si with As as said minor species, Si with P as said minor species, Si with B as said minor species, GaAs with Zn (p type) as said minor species, GaAs with S (n type) as said minor species, and GaAs with Si (n type) as said minor species.

14. An apparatus as defined in claim 4, wherein said given layer is Si with As as said minor species; and wherein said plasma generating means includes means for generating a plasma which causes said As minor species to form a species in the plasma from the group consisting of AsCl, and AsF, and As.

15. An apparatus as defined in claim 4, wherein said detecting means includes means for generating said control signal when the intensity parameter of said second frequency of radiation decreases by at least 50%.

16. An apparatus as defined in claim 15 wherein said plasma generating means includes at least one closable gas inlet into said chamber for providing a suitable gas for forming said ion plasma, and further includes an RF source for generating said plasma from said suitable gas; and wherein said controlling means controls at least said RF source in accordance with said control signal.

17. An apparatus as defined in claim 4, wherein said given layer is polycrystalline silicon heavily doped with a minor species B, and said second layer therebelow contains a B minor species therein of a concentration that is at least 50% less than in said given layer.

18. An apparatus as defined in claim 17, wherein said detecting means includes means for generating said control signal when the intensity parameter of said second frequency of radiation decreases by at least 50%.

19. An apparatus as defined in claim 18 wherein said plasma generating means includes at least one closable gas inlet into said chamber for providing a suitable gas for forming said plasma, and an RF source for generating said plasma from said suitable gas; and wherein said controlling means controls at least said RF source in accordance with said control signal.

20. An apparatus as defined in claim 4, wherein said laser beam directing means includes means for moving said laser beam to scan a predetermined volume of said plasma in said chamber.

21. An apparatus as defined in claim 4, wherein said laser beam directing means includes means for focusing said laser beam to a predetermined point in said plasma and for scanning that focused point over a plurality of predetermined volumes in said chamber; and wherein said detecting means includes means for detecting said second frequency of radiation emitted from said scanned point in said plasma.

22. An apparatus as defined in claim 21, wherein said plasma generating chamber includes at least two closable gas inlets into said chamber, each for providing a suitable gas into a different one of said plurality of predetermined volumes of said chamber for forming said plasma therein;

wherein said detecting means includes means for comparing the intensity of said second frequency of radiation obtained for each of said focused points in a given one of said plurality of predetermined volumes in said plasma to a reference value and generating a signal indicative of this comparison as said control signal; and wherein said controlling means includes means for regulating the amount of gas provided to said given one of said plurality of predetermined volumes by its respective gas inlet in accordance with said control signal.

23. A method for automatically controlling the etching of an integrated circuit wafer in the chamber of a reactive ion etching reactor when a given layer of radiation as said pumped minor species decays to a said wafer is etched through to a second layer therebelow, wherein said given layer and said second layer have different concentrations of a minor species, with the larger concentration thereof being less than or equal to 10% of either of the wafer layers by weight, comprising the steps of:

etching said wafer in said etching reactor with an etching ion plasma suitable for etching said given layer through to said second layer and for causing said minor species to enter said plasma, wherein when said given layer is etched through to said second layer, the concentration or said minor species changes;

directing a laser beam through said plasma in said chamber, with said laser beam having a first frequency suitable for pumping said minor species in said plasma to an excited energy state thereof, with said pumped minor species in said excited energy state then emitting a second frequency of radiation as said pumped minor species decays to a lower energy state;

detecting said second frequency of radiation in said chamber;

generating a control signal when a change in a parameter of said second frequency of radiation is detected, thereby indicating that said given layer has been etched through to said second layer; and changing the plasma generation in said chamber in accordance with said control signal.

24. A method as defined in claim 23, wherein said etching step comprises the step of generating said suitable plasma by applying RF energy into a suitable gas in said etching reactor; and 25. A method as defined in claim 23, wherein said laser beam directing step comprises pulsing said laser beam through said plasma; and wherein said detecting step comprises detecting for said second frequency of radiation only for a predetermined time period after initiation of each laser beam pulse.

26. A method as defined in claim 25, wherein said etching step comprises the step of etching a wafer with a given layer of Al film with a Cu minor species, and with a second layer which does not contain Cu.

27. A method as defined in claim 26, wherein said etching step includes the step of etching with a plasma containing Cl; and
wherein said laser beam directing step includes the step of directing said laser beam with a first frequency which is suitable for pumping a Cu minor species of $[CuFl]_x$ to an upper energy state.

28. A method as defined in claim 27, wherein said control signal generating step includes the step of generating said control signal when the intensity parameter of said second frequency of radiation decreases to less than 5% of its initial value.

29. A method as defined in claim 28, wherein said etching step comprises the step of generating said suitable plasma by applying RF energy into a suitable gas in said etching reactor; and
wherein said plasma generation changing step comprises stopping the application of said RF energy to said suitable gas in said etching reactor in accordance with said control signal.

30. A method as defined in claim 25, wherein said etching step comprises the step of etching a given layer of $SiO_2$ without Al doping and with a second layer thereunder including a plurality of Al studs therein which contact the bottom surface of said $SiO_2$ layer, with Al comprising said minor species to be monitored.

31. A method as defined in claim 30, wherein said etching step comprises the step of etching with a plasma containing F; and
wherein said laser beam directing step comprises the step of directing said laser beam with a first frequency which is suitable for pumping a minor species of AlF to an upper energy state.

32. A method as defined in claim 31, wherein said control signal generating step comprises the step of generating said control signal when the intensity parameter of said second frequency of radiation increases to a constant value.

33. A method as defined in claim 32, wherein said etching step comprises the step of generating said suitable plasma by applying RF energy into a suitable gas in said etching reactor; and
wherein said plasma generation changing step comprises stopping the application of said RF energy to said suitable gas in said etching reactor in accordance with said control signal.

34. A method as defined in claim 25, wherein said etching step comprises the step of etching a given layer chosen from the group consisting of Si with As as said minor species, Si with P as said minor species, Si with B as said minor species, GaAs with Zn (p type) as said minor species, GaAs with S (n type) as said minor species, and GaAs with Si (n type) as said minor species.

35. A method as defined in claim 25, wherein said etching step comprises the step of:
etching a given layer of Si with As as said minor species by generating a plasma which causes said As minor species to form a species in the plasma from the group consisting of AsCl, AsF, and As.

36. A method as defined in claim 35, wherein said control signal generating step comprises the step of generating said control signal when the intensity parameter of said second frequency of radiation decreases by at least 50%.

37. A method as defined in claim 36, wherein said etching step comprises the step of generating said suitable plasma by applying RF energy into a suitable gas in said etching reactor; and
wherein said plasma generation changing step comprises stopping the application of said RF energy to said suitable gas in said etching reactor in accordance with said control signal.

38. A method as defined in claim 25, wherein said etching step comprises the step of etching a given layer of polycrystalline silicon heavily doped with a minor species B and with said second layer thereunder containing a B minor species therein with a concentration that is at least 50% less than that in said given layer.

39. A method as defined in claim 38, wherein said control signal generating step comprises the step of generating said control signal when the intensity parameter of said second frequency of radiation decreases by at least 50%.

40. A method as defined in claim 39, wherein said etching step comprises the step of generating said suitable plasma by applying RF energy into a suitable gas in said etching reactor; and
wherein said plasma generation changing step comprises stopping the application of said RF energy to said suitable gas in said etching reactor in accordance with said control signal.

41. A method as defined in claim 25, wherein said laser beam directing step includes the step of moving said laser beam to scan a predetermined volume of said plasma in said chamber.

42. A method as defined in claim 25, wherein said laser beam directing step includes the step of focusing said laser beam to a predetermined point in said plasma and scanning that focused point over a plurality of predetermined volumes in said chamber; and
wherein said detecting step includes the step of detecting said second frequency of radiation emitted from said scanned point in said plasma.

43. A method as defined in claim 42, wherein said etching step includes the step of directing a suitable gas for generating said plasma into said etching reactor by means of at least two closable gas inlets thereinto, with each gas inlet providing said suitable gas into a different one of said plurality of predetermined volumes in said chamber for forming said plasma therein;
wherein said detecting step includes the step of comparing the intensity of said detected second frequency of radiation of said focused points in a given one of said plurality of predetermined volumes in said plasma to a reference value;
wherein said control signal generating step includes the step of generating a signal indicative of the comparison as said control signal; and
wherein said plasma generation changing step includes the step of regulating the amount of gas provided to said given one of said plurality of predetermined volumes by its respective gas inlet in accordance with said control signal.

* * * * *